:::: {.columns}
::: {.column}
United States Patent [19]
LaRossa et al.

[54] ANALYTICAL ELEMENT AND METHOD FOR ALKALINE PHOSPHATASE ASSAY

[75] Inventors: Denise D. LaRossa, Rochester; Allen L. Thunberg, Pittsford; Gary E. Norton, Rochester; Glen M. Dappen, Webster, all of N.Y.

[73] Assignee: Eastman Kodak Company, Rochester, N.Y.

[21] Appl. No.: 517,143

[22] Filed: Jul. 25, 1983

[51] Int. Cl.$^4$ .............................................. C12Q 1/42
[52] U.S. Cl. ...................................... 435/21; 435/805
[58] Field of Search ......................... 435/4, 21, 188; 436/169, 170, 175, 176; 422/56, 57

[56] References Cited

U.S. PATENT DOCUMENTS

| | | | |
|---|---|---|---|
| Re. 30,267 | 5/1980 | Brushi | 436/170 |
| 3,425,912 | 2/1969 | Deutsch et al. | 435/21 |
| 3,466,306 | 9/1969 | Babson | 435/21 X |
| 3,891,507 | 6/1975 | Breuer | 435/14 |
| 3,905,872 | 9/1975 | Forgione | 435/21 |
| 3,992,158 | 11/1976 | Przybylowicz et al. | 422/57 |
| 4,132,598 | 1/1979 | Modrovich | 435/21 |

:::
::: {.column}

[11] Patent Number: 4,555,484
[45] Date of Patent: Nov. 26, 1985

| | | | |
|---|---|---|---|
| 4,306,020 | 12/1981 | Meiattini | 435/21 |

FOREIGN PATENT DOCUMENTS

| | | | |
|---|---|---|---|
| 2012951 | 8/1979 | United Kingdom | 435/21 |

OTHER PUBLICATIONS

Bowers et al., *Clin. Chem.*, 21, pp. 1988–1995, (1975).
McCombs et al., *Clin. Chem.*, 18, pp. 97–104, (1972).

*Primary Examiner*—Alvin E. Tanenholtz
*Assistant Examiner*—Jayme A. Huleatt
*Attorney, Agent, or Firm*—J. Lanny Tucker

[57] ABSTRACT

Disclosed herein is a dry analytical element and a method of using same for quantitatively detecting alkaline phosphatase in an aqueous liquid. The element comprises, in fluid contact, first and second reagent zones which can be self-supporting or carried on a support. The first reagent zone contains a substrate for alkaline phosphatase, e.g. p-nitrophenyl phosphate, and the second reagent zone contains a buffer which is an alkali metal or ammonium salt and has a pKa in the range of 9–11.5, e.g. an alkali metal salt of carbonic acid.

20 Claims, 1 Drawing Figure

:::
::::

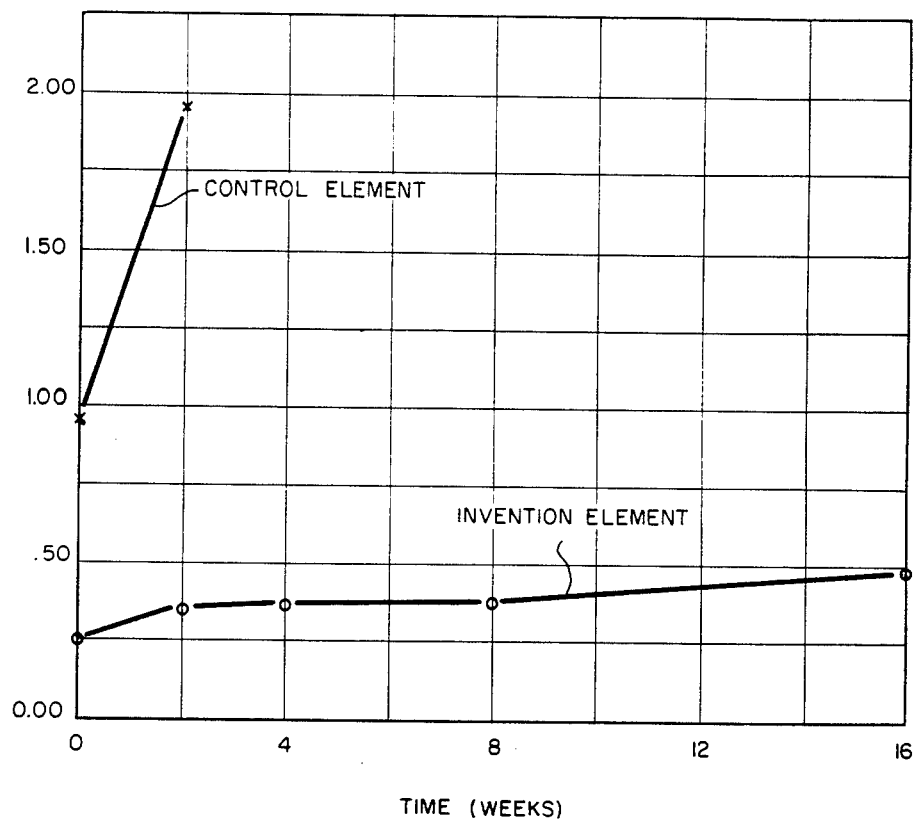

ANALYTICAL ELEMENT AND METHOD FOR ALKALINE PHOSPHATASE ASSAY

FIELD OF THE INVENTION

The present invention relates to the analysis of aqueous liquids for alkaline phosphatase content. More specifically, it relates to an analytical element and a method of using same for assaying biological fluids, e.g. blood serum, for alkaline phosphatase.

BACKGROUND OF THE INVENTION

The quantitative determination of alkaline phosphatase and isoenzymes thereof in biological fluids, and particularly in human blood serum, has become very important in the diagnosis and treatment of various physical disorders. Such determination is very important in the detection of bone and liver diseases in view of elevated concentrations of alkaline phosphatase associated with such diseases. For example, elevated alkaline phosphatase concentrations are often associated with Paget's disease, osteosarcomas, osteomalacia, obstructive jaundice, hepatitis and the like. An early and rapid detection of such elevated alkaline phosphatase concentrations can then lead to rapid treatment of the causative conditions. As a result, various assay procedures have been developed over the years to provide a quantitative determination of alkaline phosphatase.

The disodium salt of p-nitrophenyl phosphate (PNPP) is known in the art as a substrate for alkaline phosphatase assays. However, the stability of this substrate is limited because the sodium ions of the substrate accelerate spontaneous nonenzymatic hydrolysis. In U.S. Pat. No. 3,425,912 (issued Feb. 4, 1969 to Deutsch et al), reagents for use in a solution assay of alkaline phosphatase include an amine salt of PNPP, a buffer (pH 4-11), such as disodium or sodium hydrogen carbonate, and a magnesium salt activator. These reagents are made and kept together in dry form until immediately before use. While dry, the reagents are reportedly stable and have a long shelf life.

It would be desirable to have a dry test element for measuring alkaline phosphatase and thereby avoid solution assays and the use of dry powders and the problems associated therewith. As is well known, dry elements have several advantages over solution assays, including the avoiding of mixing or reconstituting reagents, minimizing sample to sample contamination or inaccuracies, their suitability for use by less skilled personnel and fewer storage requirements.

However, it has been found that when the most common and preferred reagents used in the alkaline phosphatase assay (i.e. PNPP substrate and 2-amino-2-methyl-1-propanol (2A2M1P) buffer and phosphate acceptor) are incorporated into conventional dry test elements, such as those described in U.S. Pat. No. 3,992,158 (issued Nov. 16, 1976 to Przybylowicz et al), a serious problem in pH control is encountered. Even when such elements are kept refrigerated for two weeks, a 30% loss in measured enzyme activity has been observed.

In measuring alkaline phosphatase in a liquid sample, it is essential that the pH of the sample be maintained at between about 9.7 and 10.5 for optimum enzyme activity. 2A2M1P (2-amino-2-methyl-1-propanol) is a common buffer and phosphate acceptor for alkaline phosphatase solution assays, but it has been found not to provide the needed buffering capacity in a dry element used for an alkaline phosphatase assay. When 2A2M1P is used as the buffer in a dry element, the pH tends to drift downward with time. This pH drift results in the serious loss in enzyme activity noted above.

It has been found that, in general, buffers have a pKa of 9 to 11.5 which are alkali metal or ammonium salts, can provide needed pH control in dry test elements. The use of a carbonate buffer in a dry test element for detecting alkaline phosphatase is described, for example, in U.S. Pat. No. 3,905,872 (issued Sept. 16, 1975 to Forgione). However, it has been found that the cation (e.g. sodium ions) from such buffers accelerate spontaneous nonenzymatic hydrolysis of the PNPP substrate. Such hydrolysis begins immediately when the reagents are coated to form an element and continues during storage. The end result of such substrate instability is an unwanted decline in the sensitivity of the dry element to alkaline phosphatase, which decline continues during storage.

Hence, there is a need in the art for a dry element for determining alkaline phosphatase in which the pH is easily controlled at optimum levels while simultaneously maintaining substrate stability and corresponding element sensitivity to the enzyme.

SUMMARY OF THE INVENTION

The present invention provides a dry analytical element and a method for the quantification of alkaline phosphatase in aqueous liquids. This invention overcomes the problems inherent with known alkaline phosphatase assay elements and procedures.

In particular, we have found that the dry elements of this invention exhibit excellent pH control in the optimum pH range (i.e. 8-12) for this assay over an extended period of time. Further, this pH control is obtained without sacrificing element sensitivity to alkaline phosphatase due to substrate instability. Rather, the elements of this invention have improved substrate stability and can be stored for a long time without any significant loss in enzyme activity. These important improvements are achieved by separating certain reagents in the element prior to use, i.e. the substrate for alkaline phosphate is kept separated from the buffer prior to use.

In accordance with this invention, a dry analytical element for the quantitative determination of alkaline phosphatase in an aqueous liquid comprises, in fluid contact, first and second reagent zones. The first reagent zone contains a substrate for alkaline phosphatase and the second reagent zone contains a buffer which is an alkali metal or ammonium salt and has a pKa in the range of from about 9 to 11.5.

This invention also provides a method for the quantification of alkaline phosphatase in an aqueous liquid. This method comprises the steps of: (A) physically contacting a sample of the liquid and the element described above to produce a quantifiable change; and (B) quantitatively detecting that change.

BRIEF DESCRIPTION OF THE DRAWING

The FIGURE is a graphical plot of background density versus time (weeks) for both an element of this invention and a control element outside the scope of this invention.

DETAILED DESCRIPTION OF TNHE INVENTION

The present invention relates to the quantification of alkaline phosphatase in aqueous liquids. The practice of this invention can be accomplished with biological fluids, e.g. whole blood, plasma, sera, lymph, bile, urine, spinal fluid, sputum, sweat and the like of humans or animals. It is possible also to use fluid preparations of human or animal tissue such as skeletal muscle, heart, kidney, lungs, brains, bone marrow, skin and the like. The preferred biological fluid for practice of this invention is human blood serum. The serum in most cases need not be diluted, but can be diluted for optimum results if the amount of alkaline phosphatase is unusually high. The serum can then be diluted with high protein solutions such as human or animal sera.

In the practice of this invention, alkaline phosphatase is measurable because of its function represented in the following equation which is used for illustrative purposes and which involves a typical phosphatase substrate:

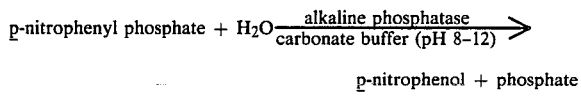

p-nitrophenol + phosphate

The p-nitrophenol can be colorimetrically detected thereby allowing quantification of the enzyme.

One or more of a variety of alkaline phosphatase substrates can be used in the practice of this invention. Such substrates generally have a phosphate group which is cleaved from the substrate molecule during the enzymatic reaction, such as an organic mono- or diester of phosphoric acid or salt thereof. Examples of useful substrates include p-nitrophenyl phosphate, phenolphthalein monophosphate, phenolphthalein diphosphate, thymolphthalein monophosphate, indoxyl phosphate, phenyl phosphate, α-naphthol phosphate, β-naphthol phosphate, β-glycerol phosphate, o-carboxyphenyl phosphate, o-methylfluorescein phosphate, alkali metal or ammonium salts thereof and others known in the art (see, e.g. U.S. Pat. No. 3,425,912, noted hereinabove). A preferred substrate is p-nitrophenyl phosphate.

Buffers useful in the practice of this invention are alkali metal or ammonium salts having a pKa of between about 9 and about 11.5. Preferably, the buffers have a pKa in the range of from about 9.5 to about 11. Useful buffers include alkali metal and ammonium salts of boric and carbonic acids; alkali metal and ammonium salts of cyclohexylaminopropane sulfonic and cyclohexylaminoethane sulfonic acids and the like. These buffers can be used singly or in mixtures. Particularly useful buffers are the alkali metal salts of carbonic acid, such as disodium carbonate, dipotassium carbonate, sodium hydrogen carbonate, potassium hydrogen carbonate, etc. Disodium carbonate is a preferred buffer.

It is preferred, but optional, that the elements of this invention also contain one or more phosphate acceptors. In the art, such a compound is also known as a transphosphorylatable buffer because, in solution assays, it acts as a buffer as well as an acceptor for the phosphate moiety cleaved from the substrate. Useful phosphate acceptors include amino alcohols or derivatives thereof, or aliphatic amines with the amino alcohols being particularly useful. Examples of useful acceptors are 2-amino-2-methyl-1-propanol, 2-dimethylamino ethanol, 2-amino-2-methyl-1,3-propanediol, 2-amino-2-ethyl-1,3-propanediol, 3-dimethylamino-1,2-propanediol, 2-methylamino ethanol, 2-isopropylamino ethanol, 2-ethylamino ethanol, tris(hydroxymethyl)amino methane, tris(2-amino-2-hydroxymethyl)propane-1,3-diol, cyclohexyl amine, diethanolamine and others known in the art. A preferred phosphate acceptor is 2-amino-2-methyl-1-propanol.

The reagents described hereinabove are incorporated into a dry analytical element of a suitable format. Typical dry element formats are known in the art and described, for example, in U.S. Pat. Nos. 3,992,158 (issued Nov. 16, 1976 to Przybylowicz et al); 4,042,335 (issued Aug. 16, 1977 to Clément); 4,144,306 (issued Mar. 13, 1979 to Figueras); 4,132,528 (issued Jan. 2, 1979 to Eikenberry et al); 4,050,898 (issued Sept. 27, 1977 to Goffe et al); 4,258,001 (issued Mar. 24, 1981 to Pierce et al); and Re. 30,267 (issued May 6, 1980 to Bruschi), the disclosures of which are incorporated herein by reference.

The elements of this invention can take the form of test papers or dry test indicators as known in the art, e.g. as disclosed in U.S. Pat. No. 3,905,872, noted hereinabove.

The dry analytical elements of this invention have at least two reagent zones containing the reagents described hereinabove. The first reagent zone contains the substrate for alkaline phosphatase and the second reagent zone contains the buffer having a pKa between 9 and 11.5 described hereinabove. These zones can be self-supporting (i.e. composed of materials rigid enough to maintain their integrity), but preferably they are carried on a suitable support. Such a support can be any suitable dimensionally stable, and preferably, transparent (i.e. radiation transmissive) material which transmits electromagnetic radiation of a wavelength between about 200 and 900 nm. Useful support materials include polystyrenes, polyesters (e.g. poly(ethylene terephthalate)), polycarbonates, cellulose esters, etc. Preferably, the first reagent zone is adjacent the support. The zones are in fluid contact with each other, meaning that fluids and reagents and reaction products in the fluids can pass between superposed regions of adjacent zones. Stated in another manner, fluid contact refers to the ability to transport components of a fluid between the zones in fluid contact. Preferably, the zones are separate coated layers, although one or more zones can be in a single layer of an element.

The reagent zones also comprise one or more matrix materials in which the reagents (i.e. reactive compounds, buffers, etc.) are distributed, i.e. dissolved or dispersed. Useful matrix materials can include hydrophilic materials including both naturally occurring substances like gelatin, gelatin derivatives, hydrophilic cellulose derivatives, polysaccharides, such as dextrose, gum arabic, agarose, etc.; cellulosic materials such as those found in filter papers or Avicel TM (commercially available from FMC Corporation, located in Philadelphia, Pa.); inorganic particulate materials, such as titanium dioxide, barium sulfate and the like; and synthetic polymeric materials e.g. homopolymers such as poly(vinyl alcohol), poly(vinyl pyrrolidone), acrylamide polymers, cellulose esters and the like, and copolymers, e.g. poly(acrylamide-co-2-hydroxyethylmethacrylate), poly(acrylamide-co-N-vinyl-2-pyrrolidone-co-2-acetoacetoxyethyl methacrylate), poly(acrylamide-co-2-hydroxyethyl acrylate), poly(acrylamide-co-2-acetoacetoxyethyl methacrylate-co-2-[N,N,N-trimethyl ammonium]ethyl methacrylate methosulfate), and others known to one skilled in the art. A preferred matrix material is gelatin. The matrix material is present in a coverage known in the art.

It is essential that the buffer useful in this invention and the alkaline phosphatase substrate be kept separate during formation of the element and prior to its use in an alkaline phosphatase assay. After the element is formed and prior to its use, the reagents in the separate reagent zones do not mix but remain in their respective zones. However, during the formation of the element by conventional coating means, when the individual zones are being laid down, for example, as coated layers, each zone must be coated in such a way that its reagents do not pass into another zone above or below it. One way this can be accomplished is by coating adjacent zones (or layers) out of different solvents such that the reagents of one zone are not soluble in the solvents of adjacent zones.

One or both of the reagent zones can act as a spreading zone. Additionally, or alternatively, the element can have one or more separate spreading zones. A spreading zone is generally a layer which can accept a liquid sample. When the liquid sample is applied directly to the layer or provided to it from a layer or layers in fluid contact with it, the sample is distributed such that a uniform apparent concentration of alkaline phosphatase is provided at the surface of the spreading layer facing the adjacent layer. Useful materials for preparing spreading zones are described, for example, in U.S. Pat. Nos. 3,992,158 and 4,258,001, noted hereinabove; and 4,292,272 (issued Sept. 29, 1981 to Kitajima et al); and U.K. Patent Application No. 2,052,057 (published Jan. 21, 1981). The spreading zone, for example, can be composed of either fibrous or non-fibrous materials, or both. Preferably, the spreading zone is an isotropically porous spreading layer comprising barious sulfate and cellulose acetate as described in U.S. Pat. No. 3,992,158, noted hereinabove.

The elements of this invention can also optionally include additional zones having specialized functions, e.g. improving analysis capability or making element manufacture more convenient. For example, it is common practice to use additional zones to promote or control adhesion between other zones. Such zones are commonly referred to as "binder" zones or "subbing" zones and are well known in the art. Such subbing zones generally contain one or more naturally-occurring or synthetic polymeric materials including gelatin or other naturally-occurring colloids; or homo- and copolymers, such as poly(acrylamide), poly(vinyl pyrrolidone), poly(n-isopropylacrylamide), poly(acrylamide-co-N-vinyl-2-pyrrolidone) and similar copolymers. Often, when such a subbing zone contains primarily gelatin, it is known as a "gel pad" zone. Such gel pads often contain one or more suitable hardeners and surfactants as known in the art.

The coverage of each reagent used in the elements of this invention can be varied broadly depending upon the liquid to be assayed. For example, the buffer having a pKa in the range of from 9 to 11.5 described hereinabove is generally present in a coverage of up to about 6 g/m$^2$, and preferably from about 2 to about 5 g/m$^2$. The substrate for alkaline phosphatase is generally present in a coverage of up to about 5 g/m$^2$, and preferably from about 0.3 to about 3 g/m$^2$. The optional phosphate acceptor, when used, is generally present in a coverage of up to about 5 g/m$^2$, and preferably from about 0.5 to about 2 g/m$^2$. The acceptor can be present in one or more layers of the element, including the reagent, spreading or subbing layers. Preferably, it is in the layer containing the buffer having a pKa between about 9 and about 11.5.

One or more zones (or layers) of the elements of this invention can contain a variety of one or more other desirable, but optional components, including surfactants, enzyme activators, or solvents, etc. These components can be present in amounts known to one skilled in the art.

Suitable surfactants useful in the elements include the nonionic alkylaryl-polyether alcohols commercially available, for example, under the Triton ™ mark from Rohm & Haas, Philadelphia, Pa.; sodium alkyl naphthalene sulfonate sold as Alkanol ™ XC by DuPont, Wilmington, Del.; mixtures of polydimethylsiloxane and polymethylphenylsiloxane, sold as DC-510 ™ by Dow Corning, Midland, Mich.; polyoxyethylene(20)oleyl ether marketed as Brij 98 ™ by ICI America, Wilmington, Del.; (p-isonoylphenoxy)polyglycidol available as Surfactant 10G ™ from Olin Mathieson Corp., Stamfor, Conn.; and others known to one skilled in this art.

Useful enzyme activators include divalent cations, such as $Mg^{++}$, $Co^{++}$, $Mn^{++}$, $Ca^{++}$, $Zn^{++}$, $Sr^{++}$, $Fe^{++}$ and the like, available in a salt form (e.g. aspartate, acetate, chloride, sulfate, etc.).

In one embodiment, an element of this invention comprises a support having thereon, in order and in fluid contact:
a first reagent layer containing a buffer which is an alkali metal or ammonium salt and has a pKa between about 9 and about 11.5 and a phosphate acceptor;
a subbing layer;
a second reagent layer containing the substrate for alkaline phosphatase; and
a spreading layer.

In another embodiment, an element comprises a support having thereon, in order and in fluid contact:
a first reagent layer containing the substrate for alkaline phosphatase;
a subbing layer;
a second reagent layer containing a buffer which is an alkali metal or ammonium salt and has a pKa between about 9 and about 11.5 and a phosphate acceptor; and
a spreading layer.

In yet another embodiment, an element comprises a support having thereon, in order and in fluid contact:
a first reagent layer containing a buffer which is an alkali metal or ammonium salt and has a pKa between about 9 and about 11.5;
a second reagent layer containing the substrate for alkaline phosphatase; and
a reagent/spreading layer containing the phosphate acceptor.

In still another and a preferred embodiment, an element comprises a support having thereon, in order and in fluid contact:
a first reagent layer containing a substrate for alkaline phosphatase;
a subbing layer; and
a second reagent/spreading layer containing a buffer which is an alkali metal or ammonium salt and has a pKa between about 9 and about 11.5 and a phosphate acceptor. The reagent/spreading layer thereby serves as both a reagent and a spreading layer.

A variety of different elements, depending on the method of assay, can be prepared in accordance with the present invention. Elements can be configured in a variety of forms, including elongated tapes on any desired width, sheets or smaller chips.

The analytical method of this invention can be manual or automated. In general, the amount of alkalin phosphatase in a liquid suspected of containing that enzyme is determined by taking the element from a supply roll, chip packet or other source and physically contacting it with a sample of the liquid. Such contact can be accomplished in any suitable manner, e.g. dipping or immersing the element into the sampler or, preferably, by spotting the element by hand or machine with a drop of the sample by pipette or other suitable dispensing means.

After sample application, the element is exposed to any conditioning, such as incubation, heating or the like, that may be desirable to quicken or otherwise facilitate obtaining any test result.

The alkaline phosphatase, if present, then catalyzes reaction of the substrate at a rate based on the concentration of alkaline phosphatase in the sample and the rate of detectable color change due to formation of the reaction product is quantifiable by passing the element through a zone in which suitable apparatus for reflection or transmission spectrophotometry is provided. By detectable color change is meant either a shift in spectral absorbance, the formation of a color where before it was colorless or a change in optical density. Suitable spectrophotometric apparatus and procedures are known in the art.

Other suitable detection means include the use of fluorescence spectrophotometry, radiometry, enzyme labeling and the like.

For example, when p-nitrophenyl phosphate is used as the substrate, the enzymatic reaction produces p-nitrophenol which is measurable at 400 nm using a conventional spectrophotometer. The rate of the quantifiable change (e.g. color change) can then be directly related to the rate of substrate reaction which, in turn, is directly related to the concentration of alkaline phosphatase in the sample.

The following examples are provided to illustrate the practice of the invention.

EXAMPLE 1

Effect of Carbonate Buffer in Dry Alkaline Phosphatase Element

This is a comparative example illustrating the improved pH control of an element having a sodium carbonate buffer compared to an element buffered with 2-amino-2-methyl-1-propanol (2A2M1P). This example also illustrates the poor substrate stability of an element containing sodium carbonate buffer and substrate wherein those reagents are not separated.

Part A

To demonstrate the improved pH control obtained by using a carbonate buffer in dry analytical elements for determining alkaline phosphatase, two dry elements were prepared by coating two samples (A and B) of poly(ethylene terephthalate) film support with the composition noted below, except that Sample B additionally contained disodium carbonate (3.4 g/m$^2$). The coated composition were dried to form a reagent layer on each support.

Reagent Compositions p-Nitrophenyl phosphate (0.3–3 g/m$^2$)
2-Amino-2-methyl-1-propanol (1–4 g/m$^2$)
Triton TM X surfactant (0.1–0.25 g/m$^2$)
Poly(acrylamide-co-2-hydroxyethyl acrylate (85:15 weight ratio) (5–15 g/m$^2$)

A spreading layer comprising microcrystalline cellulose (Avicel TM) was formed over the reagent layer of each sample element.

The surface pH of each sample element was measured just after element formation and after two weeks keeping at 25° C. (78° F.) and 50% relative humidity. The results of these keeping tests are given in Table I below. These results demonstrate the improved pH control provided by the disodium carbonate buffer in the Sample B element.

TABLE I

| | Surface pH | | |
|---|---|---|---|
| | Fresh | After two weeks keeping | Change |
| Sample A | 10.17 | 9.44 | 0.73 |
| Sample B | 10.51 | 10.34 | 0.17 |

Part B

The elements described in Part A hereinabove were also evaluated for substrate stability after element formation (fresh) and after two weeks keeping at 25° C. (78° F.) and 50% relative humidity. The background density results of these keeping tests, given in Table II hereinbelow demonstrate that the presence of carbonate buffer in Sample B greatly increases substrate instability over what normally occurs with time. Background densities were obtained by spotting the elements with about 10 μl of water or zero-level calibrator fluids, i.e. calibrator fluids which have been heat-treated to render them free of enzymes. The densities were then measured using a conventional spectrophotometer by reading the absorbance of the spotted element at 400 nm.

TABLE II

| | Background Density | | |
|---|---|---|---|
| | Fresh | After two weeks keeping | Change |
| Sample A | 0.338 | 0.461 | 0.123 |
| Sample B | 0.464 | 0.970 | 0.506 |

Part C

The improved substrate stability of an element in which sodium carbonate buffer and the substrate are separated compared to an element wherein those reagents are not separated is shown hereinbelow.

Two dry analytical elements were prepared eah having the following structure and composition.

| | | |
|---|---|---|
| Reagent/ | Barium sulfate | (108 g/m$^2$) |
| Spreading Layer | Cellulose acetate | (8.5 g/m$^2$) |
| | Polyurethane | (1 g/m$^2$) |
| | Nonionic surfactant | (2.15 g/m$^2$) |
| | p-Nitrophenyl phosphate tris salt | (2.4 g/m$^2$) |
| | Tris(hydroxymethyl)amino methane | (4.8 g/m$^2$) |
| Subbing Layer | Poly(n-isopropylacrylamide) | (0.4 g/m$^2$) |
| Gel Pad | Gelatin | (1.08 g/m$^2$) |
| | Surfactant 10G TM | (0.1 g/m$^2$) |
| | Bisvinylsulfonylmethyl | (0.1 g/m$^2$) |

| | -continued | |
|---|---|---|
| Reagent Layer | ether hardener | |
| | Gelatin | (20 g/m²) |
| | Alkanol ™ XC | (0.4 g/m²) |
| | Magnesium acetate | (0.03 g/m²) |
| | Disodium carbonate | (4.3 g/m²) |
| | Poly(ethylene terephthalate) Support | |

The surface pH of the reagent/spreading layer in each element was adjusted to 10.15 with the compounds listed in Table III hereinbelow. The pH of the reagent layer adjacent to the support was similarly adjusted to 10.1 with HCl.

Background densities were measured by the procedure described hereinabove in Part B of Example 1 just after element formation (fresh). The fresh background densities are listed in Table III hereinbelow. The elements were then stored at 25° C. (78° F.) and 15% relative humidity for up to 16 weeks and measurements of background densities were periodically taken. The results of those measurements are provided in the Figure. The data of that Figure illustrate that when sodium carbonate is used to adjust the pH of the layer containing the substrate for alkaline phosphatase (p-nitrophenyl phosphate tris salt), the background density of the element rapidly increases due to nonenzymatic hydrolysis of the substrate caused by the sodium carbonate. The element in which pH was adjusted with the lithium hydroxide and the carbonate buffer was kept separate from the substrate, however, does not exhibit such substrate hydrolysis as evidenced by the relatively constant background density exhibited over a long keeping time. Note that the background density of the control element reached the limitation of the measuring instrumentation after two weeks.

TABLE III

| | pH Adjusting Compound | Fresh Background Density |
|---|---|---|
| Control Element | Anhydrous Sodium Carbonate | 0.97 |
| Invention Element | Lithium hydroxide | 0.26 |

EXAMPLE 2

Dry Analytical Element for Determining Alkaline Phosphatase

Several dry analytical elements were prepared according to this invention and having the following structure and composition. The pH of the reagent layer was adjusted to 8.5 with lithium hydroxide during coating.

| Reagent/ | Barium sulfate | (108 g/m²) |
|---|---|---|
| Spreading Layer | Cellulose acetate | (8.6 g/m²) |
| | Polyurethane | (1 g/m²) |
| | Nonionic surfactant | (1.3 g/m²) |
| | Magnesium sulfate | (15 g/m²) |
| | 2-Amino-2-methyl-1-propanol | (1 g/m²) |
| | Anhydrous sodium carbonate | (4.3 g/m²) |
| Subbing Layer | Poly(vinyl pyrolidone) | (1.08 g/m²) |
| Reagent Layer | Gelatin | (5.4 g/m²) |
| | Bisvinylsulfonylmethyl ether hardener | (0.5 g/m²) |
| | Alkanol XC ™ | (0.06 g/m²) |
| | p-Nitrophenyl phosphate | (0.27 g/m²) |
| | tris salt | |
| Poly(ethylene terephthalate) Support | | |

The elements were stored under various conditions and background densities were measured as described in Example 1 just after element formation (fresh) and after 2- and 4-week keeping times. The results, given in Table IV hereinbelow, demonstrate the stability of these elements over four weeks after subjection to various keeping conditions.

TABLE IV

| Keeping Conditions | | Background Density (Fresh = 0.26) | |
|---|---|---|---|
| Temp. (°C.) | Relative Humidity | 2 Weeks | 4 Weeks |
| −18 | 15% | 0.27 | 0.28 |
| 6 | 15% | 0.28 | 0.28 |
| 25 | 15% | 0.32 | 0.33 |
| −18 | 50% | 0.26 | 0.27 |
| 6 | 50% | 0.26 | 0.27 |
| 25 | 50% | 0.33 | 0.36 |

The invention has been described in detail with particular reference to preferred embodiments thereof, but it will be understood that variations and modifications can be effected within the spirit and scope of the invention.

We claim:

1. A dry analytical element for the quantitative determination of alkaline phosphatase in an aqueous liquid, said element comprising a support having therein, in fluid contact, first and second reagent zones, said first reagent zone consisting essentially of a substrate for alkaline phosphatase and said second reagent zone consisting essentially of a buffer which is an alkali metal or ammonium salt and has a pKa in the range of from about 9 to about 11.5.

2. The element of claim 1 wherein said substrate is an organic mono- or diester of phosphoric acid.

3. The element of claim 2 wherein said phosphoric acid ester is p-nitrophenyl phosphate.

4. The element of claim 1 comprising a phosphate acceptor.

5. The element of claim 4 wherein said phosphate acceptor is an amino alcohol.

6. The element of claim 5 wherein said phosphate acceptor is 2-amino-2-methyl-1-propanol.

7. The element of claim 1 comprising a subbing zone between said first and second reagent zones.

8. The element of claim 1 wherein said buffer is present at a coverage of up to about 6 g/m², and said substrate is present at a coverage of up to about 5 g/m².

9. The element of claim 1 wherein said buffer is an alkali metal salt of carbonic acid.

10. A dry analytical element for the quantitative determination of alkaline phosphatase in an aqueous liquid, said element comprising a support having thereon, in fluid contact, first and second reagent zones, said first reagent zone consisting essentially of a substrate for alkaline phosphatase and said second reagent zone consisting essentially of a buffer which is an alkali metal or ammonium salt and has a pKa in the range of from about 9 to about 11.5.

11. The element of claim 10 wherein said substrate is an organic mono- or diester of phosphoric acid.

12. The element of claim 10 wherein said buffer has a pKa in the range of from about 9.5 to about 11.

13. The element of claim 10 comprising a phosphate acceptor in said second reagent zone.

14. A dry analytical element for the quantitative determination of alkaline phosphatase in a biological fluid, said element comprising a support having thereon, in order and in fluid contact, a first reagent layer consisting essentially of a buffer which is an alkali metal salt of carbonic acid; and a second reagent layer consisting essentially of p-nitrophenyl phosphate.

15. The element of claim 14 comprising a subbing layer between said first and second reagent layers.

16. The element of claim 15 wherein said second reagent layer is a spreading layer.

17. The element of claim 15 containing 2-amino-2-methyl-1-propanol.

18. A dry analytical element for the quantitative determination of alkaline phosphatase in a biological fluid, said element comprising a support having thereon, in order and in fluid contact, a first reagent layer consisting essentially of p-nitrophenyl phosphate; a subbing layer; and a second reagent layer consisting essentially of a buffer which is an alkali metal salt of carbonic acid.

19. The element of claim 18 containing 2-amino-2-methyl-1-propanol.

20. A method for the quantification of alkaline phosphatase in an aqueous liquid, said method comprising the steps of:
(A) physically contacting a sample of said liquid and an analytical element, said element comprising a support having thereon, in fluid contact, a first reagent layer consisting essentially of a substrate for alkaline phosphates; and a second reagent layer consisting essentially of a buffer which is an alkali metal or ammonium salt and has a pKa in the range of from about 9 to about 11.5, to produce a quantifiable change; and
(B) quantitatively detecting said change.

* * * * *